United States Patent [19]

Yarbrough et al.

[11] Patent Number: 5,346,485

[45] Date of Patent: Sep. 13, 1994

[54] POLYMERIC COMPOSITION FOR THE ABSORPTION OF PROTEINACEOUS FLUIDS

[75] Inventors: Sandra M. Yarbrough, Appleton; Ramakant T. Shet; Ronald S. Harland, both of Neenah, all of Wis.

[73] Assignee: Kimberly-Clark Corporation, Neenah, Wis.

[21] Appl. No.: 56,222

[22] Filed: Apr. 30, 1993

Related U.S. Application Data

[62] Division of Ser. No. 519,629, May 7, 1990.

[51] Int. Cl.$^5$ .................... A61F 13/15; A61F 13/20
[52] U.S. Cl. .................... 604/368; 604/358; 604/375; 604/376; 604/304
[58] Field of Search .............. 604/358, 368, 375, 376, 604/304, 307; 602/48–50, 52, 56

[56] References Cited

U.S. PATENT DOCUMENTS

| | | |
|---|---|---|
| Re. 31,323 | 7/1983 | Marder et al. |
| Re. 32,649 | 4/1988 | Brandt et al. |
| 2,474,306 | 6/1949 | Doub |
| 2,772,999 | 12/1956 | Masci et al. |
| 2,773,000 | 12/1956 | Masci et al. |
| 3,328,259 | 6/1967 | Anderson |
| 3,419,345 | 12/1968 | Parrish |
| 3,666,693 | 5/1972 | Chapiro et al. |
| 3,678,031 | 7/1972 | Schoggen |
| 3,805,790 | 4/1974 | Kaczmarzyk et al. |
| 3,881,490 | 5/1975 | Whitehead et al. |
| 3,897,782 | 8/1975 | Tunc |
| 4,002,173 | 1/1977 | Manning et al. |
| 4,051,086 | 9/1977 | Reid |
| 4,055,184 | 10/1977 | Karami |
| 4,084,591 | 4/1978 | Takebe et al. |
| 4,167,464 | 9/1979 | George |
| 4,173,669 | 11/1979 | Ashida et al. |
| 4,190,563 | 2/1980 | Bosley et al. |
| 4,315,507 | 2/1982 | Whitehead et al. |
| 4,381,784 | 5/1983 | Aberson et al. |
| 4,389,513 | 6/1983 | Miyazaki |
| 4,435,172 | 3/1984 | Gross |
| 4,552,938 | 11/1985 | Mikita et al. |
| 4,587,308 | 5/1986 | Mikita et al. |
| 4,634,438 | 1/1987 | Sustmann et al. |
| 4,634,439 | 1/1987 | Sustmann et al. |
| 4,654,393 | 3/1987 | Mikita et al. |
| 4,693,713 | 9/1987 | Chmelir et al. |
| 4,703,067 | 10/1987 | Mikita et al. |
| 4,732,721 | 3/1988 | Konno |
| 4,833,222 | 5/1989 | Siddall et al. |
| 4,954,562 | 9/1990 | Anderson |
| 4,959,061 | 9/1990 | Cabestany |
| 5,026,784 | 6/1991 | Le-Khac |
| 5,116,921 | 5/1992 | Hsieh |
| 5,225,506 | 7/1993 | Ahmed et al. |

FOREIGN PATENT DOCUMENTS

| | | |
|---|---|---|
| 0047009A1 | 3/1982 | European Pat. Off. |
| 0050375 | 4/1982 | European Pat. Off. |
| 0171041 | 2/1986 | European Pat. Off. |
| 2602985 | 2/1988 | France |
| 57-16033 | 1/1982 | Japan |
| 57-16034 | 1/1982 | Japan |
| 2093351A | 9/1982 | United Kingdom |

*Primary Examiner*—Randall L. Green
*Assistant Examiner*—P. Zuttarelli
*Attorney, Agent, or Firm*—Thomas J. Mielke

[57] ABSTRACT

A polymeric composition specifically adapted to absorb blood and other proteinaceous fluids and having repeating units, said polymeric composition comprising pendant neutralized carboxyl groups (salts) and pendant carboxyl groups. The polymeric composition is characterized in that the ratio of pendant neutralized carboxyl groups to pendant carboxyl groups is within the range of from about 1:9 to about 9:11, at least about 20 mole percent of the repeating units comprise a pendant neutralized carboxyl group or a pendant carboxyl group, and at least about 50 percent of the pendant neutralized carboxyl groups have been neutralized with a potassium or lithium base.

18 Claims, 4 Drawing Sheets

POLYMERIC COMPOSITION FOR THE ABSORPTION OF PROTEINACEOUS FLUIDS

This is a divisional application of copending application Ser. No. 07/519,629, filed on May 7, 1990.

BACKGROUND OF THE INVENTION

1. Field of the Invention

The present invention relates to a polymeric composition which polymeric composition is specifically adapted to absorb liquids containing dissolved or suspended proteins such as blood and menses.

2. Description of the Related Art

Water-swellable, generally water-insoluble polymeric materials are known to those skilled in the art. The use of such materials in personal care products such as diapers, feminine napkins, adult incontinent products and the like is similarly well known. As a general rule, such water-swellable, water-insoluble polymeric materials are described as being capable of being formed from a wide variety of materials over a wide range of operating conditions. Many of such polymeric materials are described as being suitable for use in personal care products designed to absorb both urine and proteinaceous fluids such as blood. Nonetheless, several references describe materials or products that are said to be particularly well adapted to absorb a specified type of body fluid.

French Pat. No. 2,602,985, published Feb. 26, 1988, is directed to absorbent polymers applied to the absorption of blood or protein-containing liquids. The described absorbent polymers have a pronounced acid character and consist of 50–95 mole percent vinyl or acrylic acid. Reference to a polymer having 50–95 mole percent acid means that a polymer formed from 100 percent acid monomer is 5 to 50 mole percent neutralized. For example, a homopolymer of acrylic acid may be formed and neutralized 5 to 50 percent, thus providing a polymer with an acid character and consisting of 50–95 mole percent of acrylic acid. The described absorbent polymers are said to be particularly well suited to absorb blood.

U.S. Pat. No. 4,693,713, issued Sep. 15, 1987, to Chmelir et al., is directed to absorbents for blood and serious body fluids. Described are mixtures of particles of a water-swellable, water-insoluble synthetic or natural polymer and an inorganic or organic water-soluble compound in the form of a pourable powder at normal temperatures. The pourable powder is said to be capable of accelerating the capillary flow of the blood through the mass of the particles. The mixtures are therefore said to be particularly suited for the absorption of blood and serious body fluids.

U.S. Pat. No. 4,055,184, issued Oct. 25, 1977, is directed to an absorbent pad comprising a finely divided mixture of a hydrolyzed starch/polyacrylonitrile graft copolymer in acidic form and a nontoxic water-soluble basic material. The presence of the basic material is described as increasing the liquid absorption capacity of the pad.

Thus, it is seen that certain polymeric compositions or structures are known, which compositions or structures are described as being specifically tailored to improve their absorption of blood or urine. Prior art references directed specifically to blood-absorbing polymeric compositions have not concerned themselves with addressing the issue of improving the intrinsic rate of absorption of said polymers. Additionally, known references have not described how to achieve maximum capacity from a particular blood-absorbing polymeric composition.

Summary of the Invention

It is desirable to provide an absorbent polymeric composition, which composition is specifically adapted to absorb proteinaceous fluids such as blood, and which polymeric composition has an improved initial rate of absorption; thus rendering it particularly well suited for use in products such as feminine napkins, wound dressings and the like. Further, it is desired to provide an absorbent polymeric composition specifically adapted to absorb proteinaceous fluids, which polymeric composition has an improved equilibrium capacity for the absorption of proteinaceous fluids such as blood, menses and polypeptide solutions.

It is further desired to provide an absorbent personal care product, such as a feminine napkin, which product contains an absorbent polymer specifically adapted to absorb proteinaceous fluids and having an improved initial rate of absorption, or an improved equilibrium capacity for the absorption of blood.

These and other related goals are achieved in a blood-swellable, generally blood-insoluble polymeric composition having repeating units, said polymeric composition comprising pendant neutralized carboxyl groups (salts) and pendant carboxyl groups. The polymeric composition is characterized in that the ratio of pendant neutralized carboxyl groups to pendant carboxyl groups is within the range of from about 1:9 to about 9:11, at least about 20 mole percent of the repeating units comprise a pendant neutralized carboxyl group or a pendant carboxyl group, and at least about 50 percent of the pendant neutralized carboxyl groups have been neutralized with a potassium or lithium base. The polymeric composition is further characterized in that it has an improved 6-minute bovine blood absorption capacity or an improved 60-minute bovine blood absorption capacity, when compared to blood-swellable, generally blood-insoluble polymeric composition having the same composition but having a ratio of pendant neutralized carboxyl groups to pendant carboxyl groups outside the range of from about 1.:9 to about 9:11, or wherein at least 50 percent of the pendant neutralized carboxyl groups have been neutralized with a sodium base.

DETAILED DESCRIPTION OF THE PREFERRED EMBODIMENTS

The present invention is directed to a blood-swellable, generally blood-insoluble polymeric composition. As used herein, a composition is considered to be blood-swellable and generally blood-insoluble when it is capable of absorbing at least about 10 grams of blood per gram of polymer and when it is substantially insoluble in blood. As used herein, reference to blood refers to bovine blood having a red blood cell hematocrit of 30 millititers of red blood cells per 100 millititers of whole blood and containing 4.8 grams of ammonium oxalate, 3.2 grams of potassium oxalate, and 150 millititers of an aqueous 0.9 weight percent sodium chloride solution per gallon of blood. While reference herein may be had to blood, it is to be understood that in the broader sense the present invention relates to polymeric compositions capable of absorbing liquids containing dissolved or suspended poolypeptides such as proteins.

Applicants have discovered that the blood absorption rate and capacity of certain polymeric compositions comprising pendant neutralized carboxyl groups and pendant carboxyl groups may be affected by at least three variables. The three variables found by the Applicants to affect the blood absorption properties of such polymeric compositions are: (1) the relative hydrophilicity of the polymeric composition; (2) the relative acidity of the polymeric composition (concentration of carboxyl groups; and (3) the base (counter ion) employed to neutralize the carboxyl groups.

The blood-swellable, generally blood-insoluble polymeric compositions of the present invention have repeating units. The polymeric composition comprises pendant neutralized carboxyl groups (salts) and pendant carboxyl groups. The polymeric composition is characterized in that the ratio of pendant neutralized carboxyl groups to pendant carboxyl groups is within the range of from about 1:9 to about 9:11. The polymeric composition is further characterized in that at least about 20 mole percent of the repeating units comprise a pendant neutralized carboxyl group or a pendant carboxyl group, and at least about 50 percent of the pendant neutralized carboxyl groups have been neutralized with a potassium or lithium base. Such a polymeric composition has an improved 6-minute bovine blood absorption capacity or an improved 60-minute bovine blood absorption capacity when compared to a blood-swellable, generally blood-insoluble polymeric composition having the same composition but having a ratio of pendant neutralized carboxyl groups to pendant carboxyl groups outside the range of from about 1:9 to about 9:11, or wherein at least 50 percent of the neutralized carboxyl groups have been neutralized with a sodium base.

In one aspect, Applicants have discovered that a polymeric composition having a high blood absorption rate (as reflected by the 6-minute bovine blood absorption capacity) or a high blood absorption capacity (as reflected by the 60-minute bovine blood absorption capacity) is achieved by providing a generally acidic polymer (ratio of neutralized carboxyl groups to carboxyl groups from about 1:9 to about 9:11) in combination with employing a potassium or lithium base to neutralize the carboxyl groups which are neutralized.

Exemplary of polymers suitable for use in the present invention are blood-swellable, generally blood-insoluble synthetic polymers having repeating units such as poly(carboxylic acids), poly(carboxylic acid anhydrides), copolymers of carboxylic acids or carboxylic acid anhydrides; and derivatives of natural polymers such as carboxymethylcellulose, carboxymethylstarch, and the like.

The polymeric compositions according to the present invention comprise repeating units. At least about 20 mole percent, desirably at least about 50 mole percent, preferably at least about 90 mole percent and most preferably at least about 99 mole percent of said repeating units comprise a pendant neutralized carboxyl group or a pendant carboxyl group. Those skilled in the art will recognize that reference to "repeating units" refers to the repeating moieties making up the backbone chain of the polymer. "Pendant" describes moieties which are attached to, but not a part of, the backbone chain.

The polymeric compositions of the present invention are desirably crosslinked. When the polymeric composition is a synthetic polymer, those skilled in the art will recognize that this crosslinking can be introduced by including a crosslinking agent in the monomer mixture from which the polymer is formed. When the polymeric composition is a derivative of a natural polymer such as carboxymethylcellulose, those skilled in the art will recognize suitable means e.g., heat-catalyzed crosslinking, of introducing a desired degree of crosslinking.

Suitable crosslinking agents for use in forming synthetic polymers according to the present invention include, without limitation, organic compounds having two or more ethylenic groups copolymerizable with the carboxyl group-containing monomer. Exemplary of suitable crosslinking agents include diacrylate or dimethacrylate of ethylene glycol; diethylene glycol; trimethylene glycol; propylene glycol; 1, 4-butane diol; 1,5-pentane diol; 1,6-hexane diol; neopentyl glycol; trimethylol propane; pentaerythritol; triacrylate or trimethacrylates of trimethylol propane and pentaerythritol; tetraacrylates or tetramethacrylates of pentaerythritol; N,N'-methylene-bis-acrylamide; N,N'-methylene-bis-methacrylamide; triallyl isocyanurate, and the like. Other suitable crosslinking agents include multivalent cations or polycations such as di-, tri-, and multi-valent cations of copper, calcium, aluminum, and the like; and polycations such as an adipic diethylene triamine polyamide epichlorohydrin resin such as that commercially available from Hercules Incorporated, Wilmington, Delaware under the trade designation Kymene™ 557 (H).

The crosslinking agent is present in the polymeric composition in an amount sufficient to cause a desired degree of crosslinking. Generally, the crosslinking agent is present in an amount of from about 0.01 to about 10.0 mole percent, preferably from about 0.1 to about 2.0 mole percent of the polymeric composition.

Methods of forming the polymeric compositions according to the present invention are known to those skilled in the art and are suitable for use in the present invention. For example, the polymeric compositions can be formed from monomer mixtures comprising carboxyl group-containing monomers, or can be formed by modification of noncarboxyl group-containing polymers. Alternatively, the polymeric compositions can be derivatives of naturally occurring polymers such as starch or cellulose.

The polymeric compositions of the present invention are characterized in that they have a ratio of pendant neutralized carboxyl groups to pendant carboxyl groups within the range of from about 1:9 to about 9:11, preferably, within the range of from about 1:3 to about 9:11. At least 50 percent, preferably at least about 80 percent, and most preferably at least about 95 percent of the neutralized carboxyl groups have been neutralized with a potassium or lithium base (counter ion).

Further, the polymeric compositions of the present invention are characterized in that they have a 6-minute bovine blood absorption capacity or a 60-minute bovine blood absorption capacity (determined as set forth below in connection with the examples) which is improved when compared to polymeric compositions having the same composition but having a ratio of pendant neutralized carboxyl groups to pendant carboxyl groups outside the range of from about 1:9 to about 9:11, or wherein at least 50 percent of the pendant neutralized carboxyl groups have been neutralized with a sodium base. It is preferred that both the 6-minute and 60-minute bovine blood absorption capacities be improved. For the purposes of this application, the 6 or 60-minute bovine blood absorption capacities for a composition according to the present invention will be considered to be improved when the capacities are at least about 10 percent, and preferably at least about 25 percent, greater than the capacities of the composition to which they are compared.

As used herein, reference to the comparison of a polymeric composition according to the present invention and a polymeric composition having the same composition but having a ratio of neutralized carboxyl groups to carboxyl groups outside the range of from about 1:9 to about 9:11, or wherein at least 50 percent of the pendant neutralized carboxyl groups have been neutralized with a sodium base will refer to the comparison when the two different polymeric compositions are tested in the same sample of bovine blood, which sample is prepared as set forth below in connection with the examples.

It is preferred that the polymeric compositions of the present invention have a 6-minute bovine blood absorption capacity determined as set forth below in connection with the examples) of at least about 14 grams of absorbed blood per gram of polymeric composition (gram per gram), preferably at least about 20 grams per gram and a 60-minute bovine blood absorption capacity (determined as set forth below in connection with the examples) of at least about 40 grams per gram, preferably at least about 50 grams per gram.

In one preferred embodiment, the blood-swellable, generally blood-insoluble polymeric compositions of the present invention are crosslinked and comprise at least about 20 mole percent of a polymerized carboxyl group-containing monomer and a crosslinking agent. Exemplary of carboxyl group-containing monomers (including associated salt monomers) suitable for use in this embodiment of the present invention are the olefinically unsaturated acids and acid anhydrides which contain at least one carbon-to-carbon olefinic double bond. Suitable olefinically unsaturated acids and acid anhydride monomers include, without limitation, acrylic acid, methacrylic acid, ethacrylic acid, maleic acid, maleic acid anhydride and mixtures thereof.

In addition to one or more of the polymerized carboxyl group-containing monomers described above, the compositions according to this preferred embodiment of the present invention may comprise a polymerized noncarboxyl group-containing monomer. Exemplary of noncarboxyl group-containing monomers which may similarly be employed in forming the polymeric compositions of the present invention are, for example, the water-soluble or water-dispersible esters of the foregoing carboxyl group-containing monomers. Suitable monomers include, without limitation, carboxylic acid or sulfonic acid ester-containing monomers, hydroxyl group-containing monomers, amide group-containing monomers, nitrile group-containing monomers and quaternary ammonium salt group-containing monomers.

The preferred carboxyl group-containing monomer for use in this preferred embodiment of the present invention is selected from the group consisting of acrylic acid and methacrylic acid.

In the preferred embodiment of the present invention described above, the polymeric composition is formed from at least about 50 mole percent, preferably from at least about 90 mole percent and most preferably from at least about 99 mole percent of a carboxyl group-containing monomer. The carboxyl group-containing monomer is preferably selected from the group consisting of acrylic acid and methacrylic acid.

Suitably, when the carboxyl group-containing monomer is water-soluble, the carboxyl group-containing monomer will be dissolved in water such that the monomer concentration is about 5 to about 70 weight percent based on total weight of the monomer-containing aqueous solution. To this monomer-containing solution is then added the crosslinking agent and, if the crosslinking agent is water-insoluble, a suitable dispersing agent known to those skilled in the art. The solution is then stirred and an initiator added. Suitable initiators are known to those skilled in the art and are, for example, selected from the group consisting of water-soluble peroxides such as potassium persulfate, sodium persulfate, ammonium persulfate, and other alkali-metal persulfates, hydrogen peroxide and water-soluble azo-compounds, and redox type initiators.

The polymerization of the solution may be initiated by elevating the temperature of the mixture containing the initiator or by using a redox-type initiator as described above. Generally, the temperature at which polymerization will begin ranges from about 15° C. to about 90° C. The exact temperatures at which the polymerization is carried out depends to a large extent on the monomers chosen and is known to those skilled in the art.

The resulting gel-like polymer is then suitably dried, ground to the desired size and subjected to a post-formation neutralization procedure. It is to be understood that the polymeric compositions of the present invention may be neutralized either in the polymerized form or when they are in the form of carboxyl group-containing monomers prior to polymerization. In either event, the carboxyl group-containing monomers or polymerized carboxyl group-containing monomers are partially neutralized by contacting with a basic solution capable of providing potassium or lithium counter ions for the neutralization. Polymeric compositions according to this preferred embodiment of the present invention have a degree of neutralization within the range of from about 10 to about 45 mole percent, preferably within the range of from about 25 to 45 mole percent.

As used herein, reference to the degree of neutralization refers to the mole percent of carboxyl groups originally present on the carboxyl group-containing monomers, which carboxyl groups have been converted to a potassium or lithium salt (pre- or post-polymerization). Those skilled in the art will recognize that reference to the degree of neutralization as defined above and reference to ratio of pendant neutralized carboxyl groups to pendant carboxyl groups refers to the same characteristic and will be used interchangeably. For example, when the polymeric composition according to the present invention is formed from a carboxyl group-containing monomer, reference to a degree of neutralization of 25 mole percent is referring to a ratio of pendant neutralized carboxyl groups to pendant carboxyl groups of 1:3. Similarly, if the polymeric compositions of the present invention are formed by derivatization of a natural polymer e.g., carboxymethylcellulose, reference to a ratio of pendant neutralized carboxyl groups to pendant carboxyl groups of 1:3 is the same as referring to a degree of neutralization of 25 mole percent.

As discussed above, a number of variables have been discovered to affect the 6 and 60-minute bovine blood absorption capacities of polymeric compositions according to the present invention. The effect of varying the variables can best be seen by reference to the following examples, including comparative examples.

EXAMPLES

In order to evaluate the blood absorption characteristics of the polymeric compositions according to the present invention, the following standard test procedures and methods are used.

Blood Preparation. To a one gallon collection vessel is added 4.8 grams of ammonium oxalate, 3.2 grams of potassium oxalate, and 150 milliliters of an aqueous 0.9 weight percent sodium chloride solution. Bovine blood is then added to the vessel until the total volume is equal to one gallon. The contents of the vessel are gently stirred to thoroughly mix. The red blood cell hematocrit of the bovine blood is then determined by centrifugation in a micro-hematocrit centrifuge. The red blood cell count is adjusted to a value within the range of from 29–31 milliliters of red blood cells per 100 milliliters of blood. If the red blood cell count is greater than 31, it is adjusted downward by the addition of bovine plasma to the blood solution. If the red blood cell count is below 29, it is adjusted upward by the addition of concentrated red blood cells. In either event, the plasma or concentrated red blood cells are isolated by placing an amount of bovine blood treated as described above in a refrigerated centrifuge. The blood is then spun to separate the red blood cells from the plasma. These two components of the blood can then be separated and employed to adjust the red blood cell count of the bovine blood sample.

The bovine blood thus prepared is employed to determine the absorption characteristics of polymeric compositions according to the present invention. Individual samples of bovine blood may vary due to variations in a number of other characteristics of the blood of a particular animal. While absolute values of blood absorption rate and capacity may vary when tested in the blood of different bovines, the relative performance remains the same. Thus, a polymeric sample according to the present invention may, for example, have a 6-minute bovine blood absorption capacity of 15 grams per gram in a first blood sample and 10 grams per gram in a second blood sample. A similar polymeric composition not within the scope of the present invention (used for comparison as discussed above) may have a 6-minute bovine blood absorption capacity of 11 grams per gram in the first blood sample and 6 grams per gram in the second blood sample. Thus, even though the absolute value (11) of the sample outside the scope of the present invention in the first blood sample may be greater than the absolute value (10) of the sample according to the present invention in the second blood sample, the condition of showing improvement is still met because the two samples must be compared in the same blood sample. Thus, the relative behavior (in the same blood sample) demonstrates an improvement (15:11, 10:6).

The following method is employed to determine the absorption characteristics of a given polymeric composition.

Determination of Blood Absorption Capacity. The polymeric composition to be tested is provided in granular form. The material is sifted on US standard size screen such that it is passed by a 50 mesh screen and retained on a 100 mesh screen. Thus, the particles have a maximum cross-sectional dimension of between about 150 and 300 microns. During the test, the polymeric composition is contained within a porous, heat-sealable paper-like material having a basis weight of about 30 grams per square meter, a thickness of about 6 mils, and a porosity such that the material will pass about 170 cubic feet of air per minute per square foot at a pressure of 0.5 pounds per square inch, which is commercially available from the Kimberly-Clark Corporation under the trade designation K-C-542 Berkshire Heat Seal. Specifically, the paper-like material is cut into 3 inch by 6 inch strips, folded in half lengthwise, and heat impulse sealed along two sides. A sample of 0.2 grams of the polymeric composition to be tested is inserted into the pouch formed by the paper-like material and the third side is sealed. A control pouch is prepared as described except it does not contain any of the polymeric composition. The control pouch is tested to determine the amount of blood which it absorbs.

To determine the absorption properties of the polymeric composition, approximately one liter of bovine blood is placed in a large open-mouthed container and warmed to 37° C. in a constant temperature bath. The pouches containing the polymeric compositions prepared as described above are gently shaken to evenly distribute the polymeric composition over one planar surface of the pouch and are then set flat. The pouches are placed in a mesh holder designed to keep the pouches submerged in a generally horizontal orientation during its exposure to the blood. The mesh holder is lowered into the warmed bovine blood and allowed to swell for the desired period of time. At the end of the desired period of time, the mesh holder is removed from the bovine blood and the samples allowed to drain for one minute before the sample weight is recorded. The grams of blood absorbed is calculated by deducting the weight of the pouch prior to insertion into the bovine blood and the weight of the blood absorbed by the pouch (as determined from the control runs) from the weight of the pouch after insertion into the bovine blood.

The test samples are generally placed in bovine blood for about 6 minutes and the amount of blood absorbed in said time period determined. Due to the relatively short period of time that the polymeric compositions are allowed to remain in contact with the blood, this initial capacity is believed to be representative of the initial rate of absorption. That is, the higher the capacity on a gram of absorbed blood per gram of polymer basis, the faster the initial rate must be to achieve such a capacity in a relatively short period of time. The test samples are then placed back in contact with the bovine blood and allowed to remain there for up to 60 minutes. After 60 minutes, all of the polymeric samples tested had reached at least about 75 percent of their total equilibrium capacity. As a general rule, if you have an improved 60-minute bovine blood absorption capacity you will have an improved equilibrium bovine blood absorption capacity.

EXAMPLE 1

An air-jacketed polymerization vessel is provided. A 1000 milliliter resin flask having four standard tapered 24/40 inlet ports is provided. The resin flask is about one inch smaller in outside diameter than the inside of a beaker mantle into which the resin flask is placed. Electric coils are present in the mantle to heat the air around the resin flask. In operation, a thermistor probe present inside the resinous flask senses the temperature of the liquid present therein. When the temperature of the liquid has reached a set point, a solenoid is activated and a stream of air sweeps the hot air present in the free space around the resin flask out of the mantle. Into the central port of the resin flask is inserted a glass agitator shaft having on one end thereof a teflon paddle and bushing with O-ring seal. The shaft is connected to a constant-speed stirrer with a short piece of rubber tubing which slips when the contents of the reactor can no longer be stirred. One of the remaining ports is employed as a nitrogen inlet. Another of the remaining ports is employed to hold a condenser with the sole remaining port having inserted therein a thermowell.

A nitrogen purge (80 cubic centimeters per minute) is started into the resin flask. To the flask is added 139.5 grams of distilled water. 1.8 grams of a nonionic surfactant commercially available from Rohm and Haas under the trade designation Triton X-102 is dissolved in 36 grams (0.5 mole) of acrylic acid. The mixture of acrylic acid and the surfactant is added to the resin flask. To the resin flask is then added 0.5 grams (0.0032 mole) N,N'-methylenebisacrylamide (MBA). Finally, 0.1 gram of sodium persulfate initiator is dissolved in 10 grams of water. The initiator is added to the reactor when the reactor contents reach 70° C. Within a few minutes, the reactor contents set to a rubbery gel. The gel is allowed to sit in the reactor undisturbed for one hour after which it is removed, cut into small pieces, and dried on a glass plate in a 70° C. convection oven overnight. The gel is found to contain 20 percent polymer by weight. The dry polymer is ground in a laboratory blender and separated on US standard screens so that it passes through a 20 mesh screen and is retained on a 100 mesh screen (150–850 microns). This sample is thenpostneutralized to the desired degree.

The postneutralization process is accomplished by dissolving the desired mole percent of potassium hydroxide in enough water to swell the polymer threefold. For example, if a 45 percent neutralization is desired, 0.45 moles of potassium hydroxide is employed per mole of acrylic acid. The polymer is added to the potassium hydroxide solution quickly, but evenly, and is hand-stirred until the solution is absorbed. The neutralized polymer is re-dried in a 70° C. convection oven and is again ground in a laboratory blender to obtain the desired 150 to 300 micron particle size desired for testing in blood.

To determine the effect of the degree of neutralization on blood and saline absorption, a variety of polymeric compositions are prepared as described above with the degree of neutralization being varied between 15 and 75 mole percent. The absorbency on a gram of absorbed fluid per gram of polymer basis is determined in bovine blood and in an aqueous solution containing 0.g weight percent sodium chloride. The results set forth in Table I are based on a 30-minute exposure to blood or saline.

TABLE 1

| Degree of Neutralization | Absorbency (g/g) | |
|---|---|---|
| | Blood | Saline |
| 15 | 45 | 15 |
| 30 | 46 | 22 |
| 45 | 48 | 24 |

TABLE 1-continued

| Degree of Neutralization | Absorbency (g/g) | |
|---|---|---|
| | Blood | Saline |
| 75* | 36 | 30 |

*Not an example of the present invention

Figure 1:
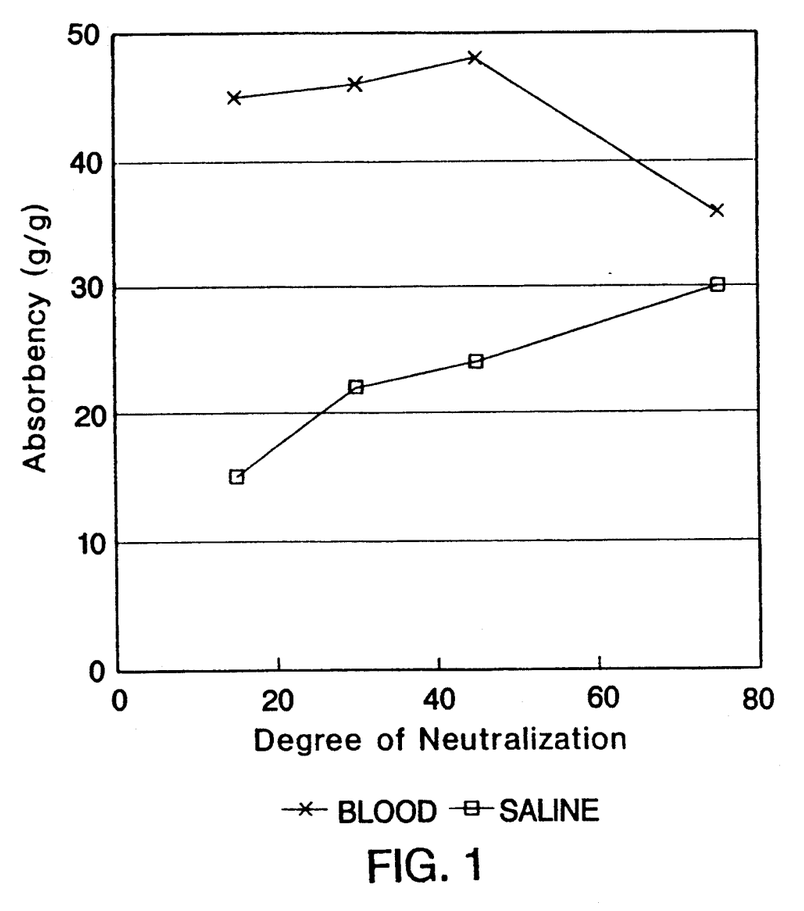
FIG. 1 is a graphic illustration of the data set forth in Table 1.

FIG. 1 illustrates the data set forth in Table 1 in graphic form. As can be seen from reference to Table 1 and FIG. 1, the absorbency in blood remains at about the same generally high level as the degree of neutralization increases from 15 percent to 45 percent. At a degree of neutralization above about 45 percent, a drop in blood absorbency is observed. However, the absorbency in a saline solution increases steadily as the degree of neutralization increases from 15 to 75 percent. Thus, when it is desired to produce an absorbent polymer specifically adapted for absorbing blood, it is desirable to have a relatively low degree of neutralization. To the contrary, when it is desired to absorb saline (which can in many ways be equated to urine), it is desirable to have a highly neutralized polymer.

Compositions according to the present invention therefore have a degree of neutralization less than about 45 mole percent based on the carboxyl groups present in the carboxyl group-containing monomers.

EXAMPLE 2

A polymeric composition is prepared as set forth in connection with Example 1 through the first drying step and prior to the post-formation neutralization process with the exception that 0.385 grams (0.0025 moles) of MBA is employed. For this example, the polymer so produced is divided into 6 portions. Each portion is then neutralized to 30 or 75 mole percent with either lithium hydroxide, sodium hydroxide, or potassium hydroxide. The blood absorption capacity is then determined at 6 minutes, 30 minutes and 60 minutes. The results of this test are set forth in Table 2.

TABLE 2

| Time | Ion | Degree of Neutralization | Absorbency (g/g)[1] | | Absorbency (g/m)[2] | |
|---|---|---|---|---|---|---|
| | | | Blood | Saline | Blood | Saline |
| 6 | Na | 30* | 15 | — | 1188 | — |
| 6 | Li | 30 | 23 | — | 1692 | — |
| 6 | K | 30 | 27 | — | 2250 | — |
| 30 | Na | 30* | 41 | 30 | 3222 | 2358 |
| 30 | Li | 30 | 53 | 29 | 3906 | 2140 |
| 30 | K | 30 | 49 | 25 | 4176 | 2085 |
| 60 | Na | 30* | 46 | 30 | 3616 | 2358 |
| 60 | Li | 30 | 54 | 29 | 3985 | 2140 |
| 60 | K | 30 | 51 | 25 | 4253 | 2085 |
| 6 | Na | 75* | 15 | — | 1328 | — |
| 6 | Li | 75* | 26 | — | 1989 | — |
| 6 | K | 75* | 23 | — | 2312 | — |
| 30 | Na | 75* | 33 | 36 | 2921 | 3186 |
| 30 | Li | 75* | 42 | 39 | 3213 | 2983 |
| 30 | K | 75* | 32 | 33 | 3216 | 3317 |
| 60 | Na | 75* | 39 | 36 | 3452 | 3186 |
| 60 | Li | 75* | 43 | 39 | 3290 | 2983 |
| 60 | K | 75* | 35 | 33 | 3518 | 3317 |

Figure 2:
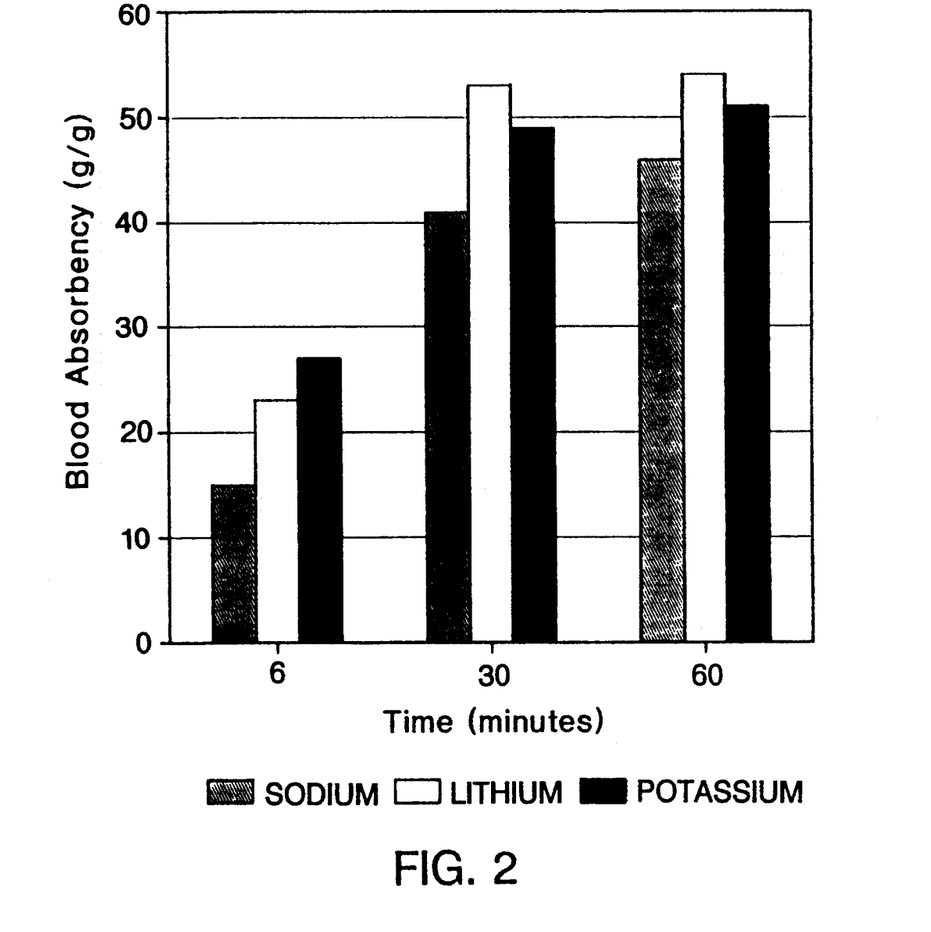
FIG. 2 is a graphic illustration of certain data set forth in Table 2.

*Not an example of the present invention
[1]Absorbency in grams of absorbed blood/saline per gram of polymer
[2]Absorbency in grams of absorbed blood/saline per mole of polymeric repeating unit FIG. 2 graphically illustrates the blood absorbency data (gram per gram) set forth in Table 2 at a degree of neutralization of 30 percent. As can be seen from reference to FIG. 2 and Table 2, the use of either lithium or potassium as the counter ion in neutralization of the polymeric compositions according to the present invention produces compositions having an improved blood absorption capacity (rate) for the tested time. With reference to Table 2, it is seen that, with respect to the absorption capacity in a saline solution, varying the counter ion does not produce the same results to the same degree as with blood absorbency. Moreover, reference to Table 2 indicates that those compositions having a degree of neutralization of 30 percent have a relatively greater difference between the absolute values of blood absorption and saline absorption; while at a degree of neutralization of 75 percent, the difference between the absolute values of blood absorption and saline absorption appear to be relatively smaller. Thus, the compositions of the present invention are again seen to be specifically adapted for the absorption of blood.

The preferred blood absorption properties achievable by carefully selecting the counter ion and controlling the degree of neutralization has not heretofore been recognized.

EXAMPLE 3

In order to determine the effect of choice of carboxyl group-containing monomer, an acrylic acid polymer is prepared as set forth in Example 1 except 0.270 grams (0.00175 mole) of MBA is employed. The acrylic acid polymer is post-neutralized with potassium hydroxide to varying degrees of neutralization. Similarly, a methacrylic acid polymer is formed, again employing the process set forth in Example 1, with the exceptions that 43 grams of methacrylic acid (0.5 mole) is substituted for the 36 grams (0.5 mole) of acrylic acid and 0.154 grams (0.001 mole) MBA is employed. Moreover, an additional 31 grams of water are added to keep the monomer concentration at 20 weight percent based on total monomer solution weight. The methacrylic acid polymer so produced is neutralized with potassium hydroxide to varying degrees of neutralization. The blood absorption characteristics are then determined for the two polymers at 6, 30, and 60 minutes. The results of these tests are set forth in Table 3.

TABLE 3

| Degree of Neutralization | 6-Minute Absorbency (g/g) | | 30-Minute Absorbency (g/g) | | 60-Minute Absorbency (g/g) | |
|---|---|---|---|---|---|---|
| | AA | MAA | AA | MAA | AA | MAA |
| 15 | 15 | 20 | 37 | 30 | 48 | 32 |
| 30 | 16 | 21 | 39 | 29 | 47 | 30 |
| 45 | 17 | 22 | 43 | 26 | 51 | 25 |

AA = acrylic acid
MAA = methacrylic acid

Figure 3:
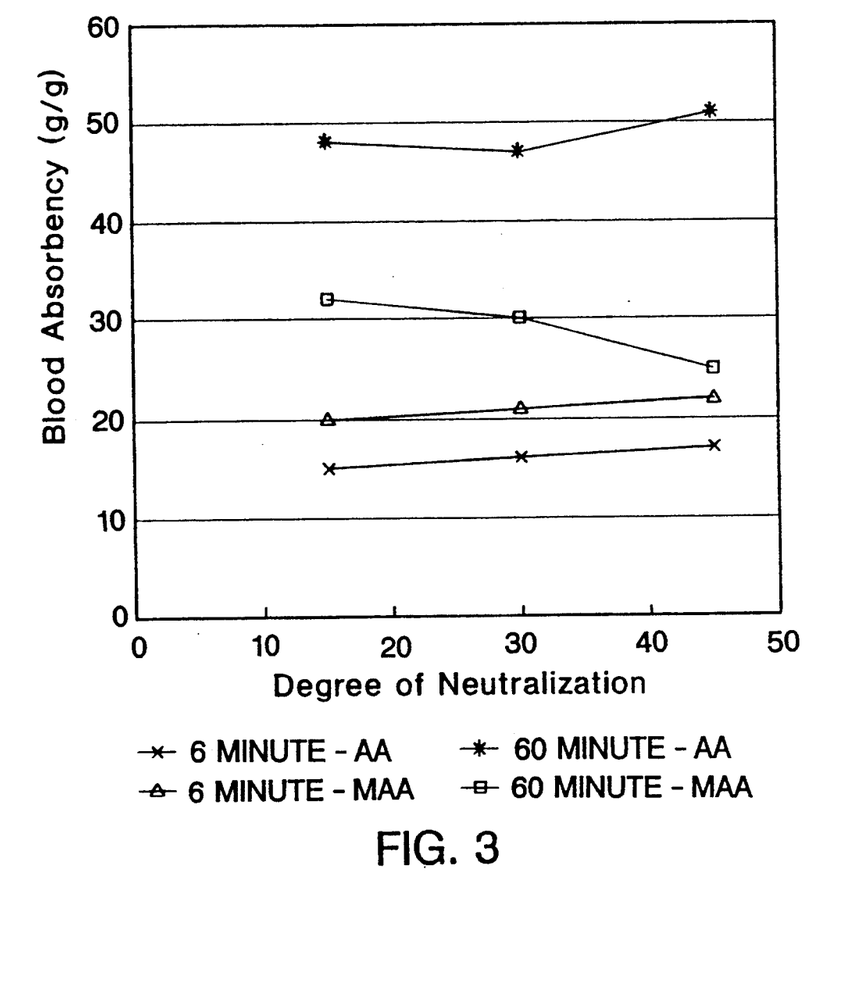
FIG. 3 is a graphic illustration of the data set forth in Table 3.

FIG. 3 graphically illustrates the 6 and 60-minute data set forth in Table 3. As can be seen from reference to Table 3, the optimum 30 and 60-minute blood absorption capacity occurs at a lower degree of neutralization when methacrylic acid is substituted for acrylic acid. It is believed that, due to the presence of a methyl group, the methacrylic acid polymer is less hydrophilic than the acrylic acid polymer. Additionally, the absorption rate (6-minute capacity) is greater for the methacrylic acid polymer than for the acrylic acid polymer.

EXAMPLE 4

To determine the effectiveness of the relative hydrophilic nature of the crosslinking agent, the following experiment is performed. An acrylic acid polymeric composition is formed as set forth in connection with Example 1 using 0.231 grams (0.0015 moles) methylenebisacrylamide (MBA) as the crosslinking agent. The polymeric composition so formed is divided into several portions, which portions are neutralized to varying degrees. Similarly, an acrylic acid polymeric composition is prepared as set forth in connection with Example 1, with the exception that 0.144 grams (0.00049 moles) of trimethylolpropanetriacrylate is substituted as the crosslinking agent for the methylenebisacrylamide described in Example 1. The trimethylolpropanetriacrylate is less hydrophilic than the methylenebisacrylamide employed in Example 1, as evidenced by the fact that the trimethylolpropanetriacrylate is relatively less water soluble than the methylenebisacrylamide. The acrylic acid polymer composition formed employing trimethylolpropanetriacrylate as a crosslinking agent is prepared and divided into several portions, which portions are neutralized to varying degrees. The blood absorption capacity of the different portions is then determined. The results of the blood absorbency testing are set forth in Table 4.

TABLE 4

| Degree of Neutralization | 6-Minute Absorbency (g/g) | | 30-Minute Absorbency (g/g) | | 60-Minute Absorbency (g/g) | |
|---|---|---|---|---|---|---|
| | TPT | MBA | TPT | MBA | TPT | MBA |
| 15 | 9 | 20 | 29 | 42 | 45 | 53 |
| 30 | 19 | 24 | 44 | 47 | 56 | 54 |
| 45 | 14 | 23 | 41 | 44 | 52 | 51 |
| 75* | 16 | 24 | 40 | 39 | 47 | 42 |

Figure 4:
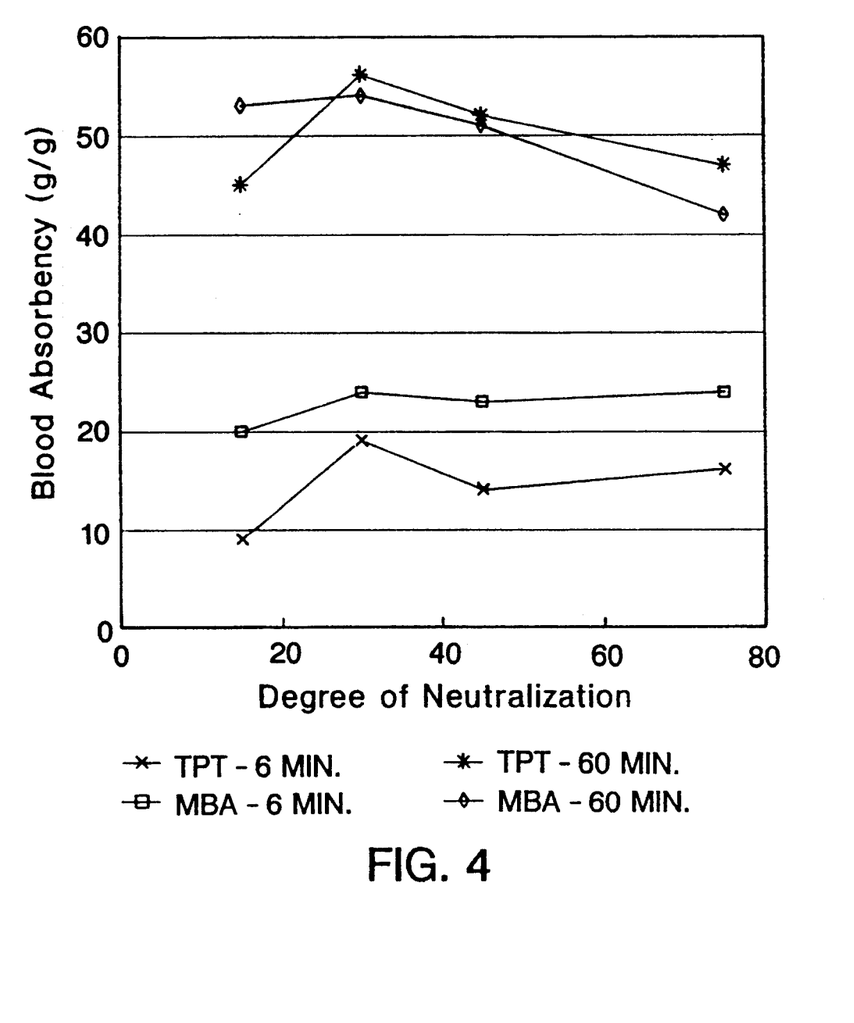
FIG. 4 is a graphic illustration of the data set forth in Table 4.

*Not an example of the present invention
TPT = trimethylolpropanetriacrylate
MBA = methylenebisacrylamide FIG. 4 graphically illustrates the 6 and 60-minute test data set forth in Table 4. As can be seen from reference to Table 4 and FIG. 4, the crosslinking agent may be either water-soluble or water-insoluble and still perform well in forming compositions according to the present invention.

Thus, while it is hypothesized that what is required for improved blood absorbency is a particular system with a balance of hydrophilic and less hydrophilic constituents, what is apparent from the examples is that the ability of a given polymeric composition to absorb blood is dependent on the degree of neutralization of the acid-groups present on the polymeric composition in connection with the counter ion employed to achieve the desired degree of neutralization. Moreover, as illustrated in the examples, the degree of neutralization required to optimize the blood absorption characteristics of such a polymeric composition is further dependent on the nature of the monomer (specifically the degree of hydrophilicity) from which the polymer is formed.

As is apparent to those skilled in the art, the absorption rate of a given polymeric composition in blood, as well as in other fluids, is dependent, at least to a degree, on the surface area of the particles involved. Accordingly, for the purpose of this application, the blood absorption values set forth herein are determined on solid, non-agglomerated polymer particles having a diameter within the range of from about 150 to about 300 microns. The use of agglomerated particles would, it is believed, exhibit a high initial capacity (rate) due to their vastly increased surface area per unit volume of material.

The blood-swellable, generally blood-insoluble polymeric compositions described are particularly well suited for use in products intended to absorb proteinaceous fluids. Exemplary of such products are feminine napkins, wound dressings, hospital gowns, drug delivery devices, biotechnology applications such as concentration of proteins, and the like.

When used in a feminine napkin, the feminine napkin will suitably comprise an outer generally moisture-impermeable cover, an absorbent structure containing the polymeric compositions according to the present invention, and an inner liner adapted to contact the skin of a wearer. The absorbent structure is located between the inner liner and the outer cover. The outer cover may comprise, for example, a film of polyethylene or polypropylene, a foam of polyethylene or polypropylene, or the like. The absorbent structure may comprise a matrix of fibers, such as cellulosic fibers, or may be a mixture of cellulosic fibers and meltblown synthetic fiber containing from about 0 to about 100 percent of synthetic meltblown fibers, such as polyethylene or polypropylene fibers. The preferred cellulosic fiber is wood pulp fluff. When synthetic fibers are present in the absorbent structures, the synthetic fibers are generally present in an amount of from about 1 to about 95 weight percent based on total weight of the absorbent structure. The blood-swellable, generally blood-insoluble polymeric compositions of the present invention are suitably present in the absorbent structure in an amount of from about 5 to about 99 weight percent and may be located in the absorbent structures in discrete locations, may be uniformly located throughout the absorbent structure and may be in the form of a layer or may be intimately mixed throughout the thickness of the absorbent structure. The body side liner is suitably formed from a nonwoven synthetic fiber such as spunbonded polyester or the like.

Exemplary of suitable feminine napkins are those described in U.S. Pat. Nos. 4,315,507 issued to Whitehead; 3,881,490 issued to Whitehead; and 3,805,790 issued to Kaczmarzyk which patents are hereby incorporated by reference.

Those skilled in the art will recognize that the present invention is capable of many modifications and variations without departing from the scope thereof. Accordingly, the detailed descriptions and examples set forth above are meant to be illustrative only and are not meant to limit in any manner, the scope of the invention as set forth in the following claims.

What is claimed is:

1. A blood-swellable, generally blood-insoluble polymeric composition comprising:
   at least about 20 mole percent based on said polymeric composition of a polymerized carboxyl group-containing monomer; and
   a crosslinking agent, said polymeric composition being characterized in that:
   (a) it has a degree of neutralization within a range of from about 10 to about 45 mole percent of said carboxyl groups,
   (b) at least 50 percent of the neutralized carboxyl groups are neutralized with a potassium or lithium base.

2. The polymeric composition according to claim 1 wherein said carboxyl group-containing monomer is selected from the group consisting of olefinically unsaturated acids and acid anhydrides which contain at least one carbon-to-carbon double bond and the associated slat monomers.

3. The polymeric composition according to claim 2 wherein said carboxyl group-containing monomer is acrylic acid.

4. The polymeric composition according to claim 1 wherein said polymeric composition is in a form of non-agglomerated, solid particles.

5. The polymeric composition according to claim 4 wherein said polymeric particles have an average maximum cross-sectional dimension within the range of from about 150 to about 300 microns.

6. The polymeric composition according to claim 1 wherein at least about 80 percent of said neutralized carboxyl groups are neutralized with a potassium or lithium base.

7. The polymeric composition according to claim 6 wherein at least about 95 percent of said neutralized carboxyl groups are neutralized with a potassium or lithium base.

8. The polymeric composition according to claim 1 wherein said polymeric composition comprises at least about 50 mole percent of a polymerized carboxyl group-containing monomero.

9. The polymeric composition according to claim 8 wherein said polymeric composition comprises at least about 90 mole percent of a polymerized carboxyl group-containing monomer.

10. A blood-swellable, generally blood-insoluble polymeric composition, said composition comprising:
    at least about 50 mole percent of a polymerized acrylic acid monomer; and
    a crosslinking agent; said polymeric composition being characterized in that it has a 6-minute bovine blood absorption capacity of at least about 14 grams per gram, a 60-minute bovine blood absorption capacity of at least about 40 grams per gram, and a degree of neutralization between about 10 and about 45 mole percent of said carboxyl groups, wherein at least about 80 percent of the neutralized carboxyl groups, are neutralized with a potassium or lithium base.

11. An absorbent product for the absorption of proteinaceous body fluids, the product comprising:
    an outer moisture-impermeable cover;
    a body side liner superposed in facing relation to said outer cover and adapted to contact the skin of a wearer; and
    an absorbent structure located therebetween, said absorbent structure comprising a blood-swellable, generally blood-insoluble polymeric composition comprising:
    at least about 20 mole percent based on said polymeric composition of a polymerized carboxyl group-containing monomer; and
    a crosslinking agent; said polymeric composition being characterized in that:
    (a) it has a degree of neutralization within a range of from about 10 to about 45 mole percent of said carboxyl groups,
    (b) at least 50 percent of the neutralized carboxyl groups are neutralized with a potassium or lithium base.

12. The absorbent product according to claim 11 wherein said absorbent structure further comprises an absorbent matrix of fibers in which said polymeric composition is dispersed in the form of solid, non-agglomerated discrete particles.

13. The absorbent product according to claim 11 wherein said absorbent matrix of fibers comprises a mixture of cellulosic fibers and meltblown synthetic polymeric fibers.

14. The absorbent product according to claim 11 wherein said carboxyl group-containing monomer is selected from the group consisting of acrylic acid, methacrylic acid, and mixtures thereof.

15. The absorbent product according to claim 14 wherein said carboxyl group-containing monomer is acrylic acid.

16. The absorbent product according to claim 15 wherein said polymeric composition has a degree of neutralization within the range of from about 25 mole percent to about 45 mole percent.

17. The absorbent product according to claim 11 wherein said polymeric composition has a 6-minute bovine blood absorption capacity of at least about 14 grams per gram.

18. The absorbent product according to claim 11 wherein said polymeric composition has a 60-minute bovine blood absorption capacity of at least about 40 grams per gram.

* * * * *